United States Patent [19]
Lichtman et al.

[11] Patent Number: 5,782,752
[45] Date of Patent: Jul. 21, 1998

[54] DEVICE FOR CARRYING TWO UNITS IN END TO END DISPOSITION AND FOR MOVING ONE OF THE UNITS ALONGSIDE THE OTHER OF THE UNITS

[75] Inventors: Philip R. Lichtman, Newton; Koichiro Hori, Framingham, both of Mass.

[73] Assignee: Vista Medical Technologies, Inc., Carlsbad, Calif.

[21] Appl. No.: 628,448

[22] Filed: Apr. 5, 1996

[51] Int. Cl.⁶ .............................. A61B 1/05; F16H 27/02
[52] U.S. Cl. .......................... 600/137; 600/129; 600/173; 74/89.17
[58] Field of Search ........................ 600/101, 106, 600/109, 112, 113, 129, 137, 166, 173; 348/65; 74/490.07, 490.1, 89.17, 479.01, 480 R, 665 A–665 E

[56] References Cited

U.S. PATENT DOCUMENTS

| | | |
|---|---|---|
| 4,832,003 | 5/1989 | Yabe . |
| 5,021,888 | 6/1991 | Kondou et al. . |
| 5,025,778 | 6/1991 | Silverstein et al. .............. 600/109 X |
| 5,166,787 | 11/1992 | Irion ............................. 348/76 |
| 5,305,121 | 4/1994 | Moll .......................... 348/65 X |

Primary Examiner—John P. Leubecker
Attorney, Agent, or Firm—Pandiscio & Pandiscio

[57] ABSTRACT

A device carries first and second units in aligned end-to-end disposition at a distal end of a shaft and provides structure for moving the second of the units into position alongside the first of the units. The device comprises a base portion to which a proximal end of the shaft is fixed, the first unit being fixed to the distal end of the shaft. A rod extends lengthwise through the shaft and a portion of the first unit, and is off-set from an axis of the shaft and fixed to the second unit removed from an axis of the second unit. Mounted on the base portion is structure for effecting rotational movement of the rod to effect rotational movement of the second unit to a position removed from alignment with the first unit, and for effecting axial movement of the rod to effect axial movement of the second unit into the position alongside the first unit.

25 Claims, 4 Drawing Sheets

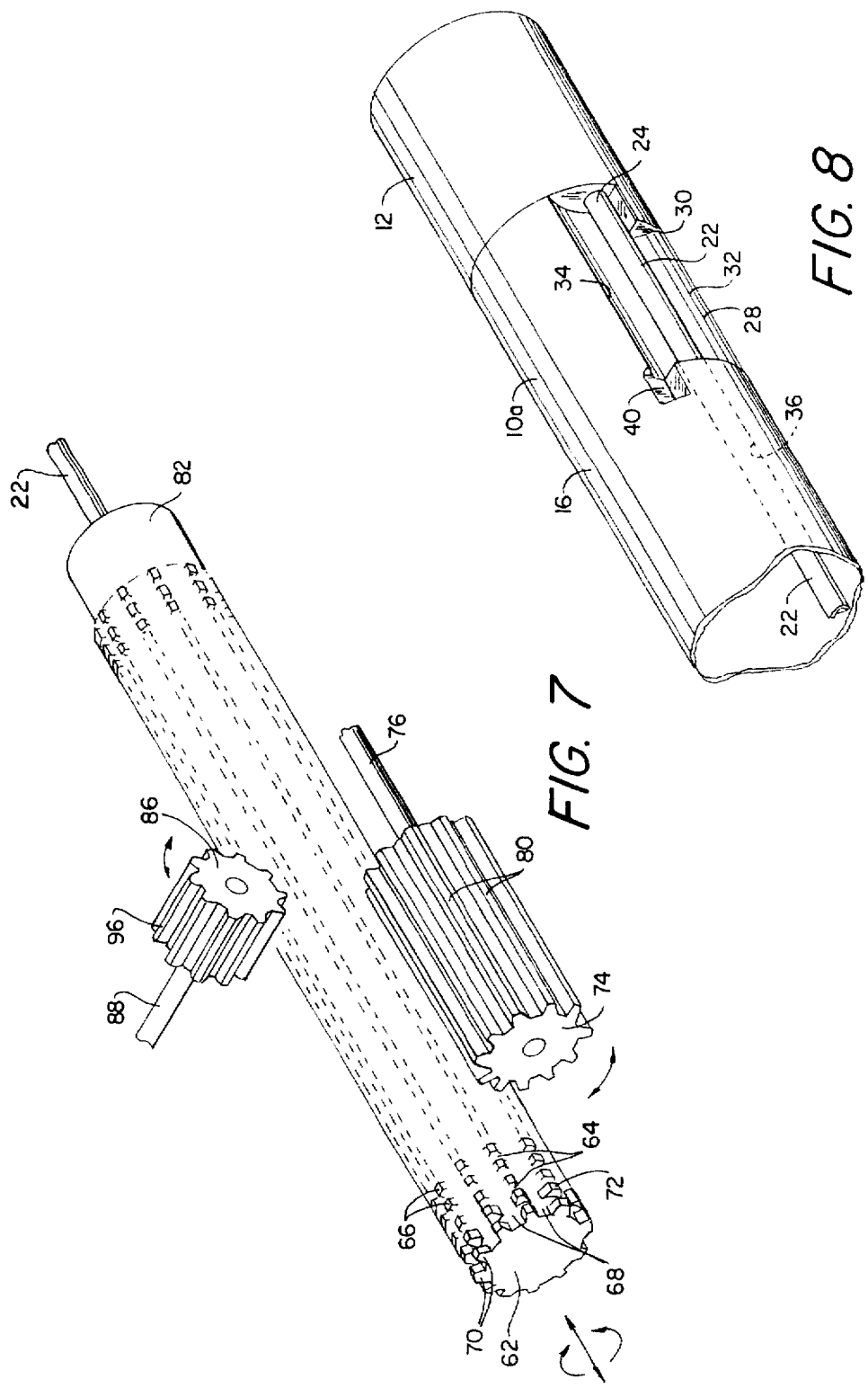

DEVICE FOR CARRYING TWO UNITS IN END TO END DISPOSITION AND FOR MOVING ONE OF THE UNITS ALONGSIDE THE OTHER OF THE UNITS

BACKGROUND OF THE INVENTION

1. Field of the Invention

The invention relates to mechanical devices for carrying a plurality of units in a first disposition and moving at least one of the units to a second disposition relative to at least one other of the units, and is directed more particularly to a device for supporting and carrying two units end-to-end and for moving one of the units alongside the other of the units.

2. Description of the Prior Art

There are instances in which it is desired to mount and carry units in tandem for passing the units through as small an orifice as possible in a boundary layer and then rearranging the units in a side-by-side relationship.

In the field of medical instruments, for example, it is beneficial in endoscopic examination and in surgery to introduce two or more units serially through a relatively small orifice and, once inside the body, reposition the units side-by-side, a disposition of units which, if inserted initially, would require an orifice twice as large, or more, than the small orifice required for introduction of the units in tandem.

In endoscopes, it is known to provide an electronic optical image sensor (hereinafter also referred to as a video device) at the distal end of the endoscope shaft. Such video devices are shown and described in U.S. Pat. No. 4,832,003, issued May 23, 1989, in the name of Hisao Yabe; in U.S. Pat. No. 5,021,888, issued Jun. 4, 1991, in the name of Yuu Kondau, et al; and in U.S. Pat. No. 5,166,787, issued Nov. 24, 1992, in the name of Keaus Ission. In the field of endoscopes, it would be beneficial to provide an endoscope shaft with two or more electronic image sensors which could be introduced into the body serially and, once inside the body, rearranged to side-by-side positions, such that two or more images could be transmitted to provide to an operator a stereoscopic view of the body portion under examination.

In surgery, it is desirable to limit the size of an incision required for introduction of surgical tools and for viewing of the area of concern. It would be beneficial to have available an instrument by which two units could be introduced serially through an orifice of limited size, with one of the units carrying the required tool and the other unit movable to a position alongside the first unit and carrying image sensing means for providing a view of the tool in operation.

Such an instrument could prove beneficial in any application or area of use wherein it is desired to limit the size of an orifice through a boundary layer, to pass two or more units through the orifice and, thereafter, to position the units side-by-side. Thus, for example, it is desired and often necessary to severely limit the size of any orifice in the pressure hull of deep underwater vehicles. It also is desirable to use acoustic sensors on such vehicles for determining range, with at least two sensors being required for purposes of triangulation and thereby determination of range. It is recognized that a device adapted to pass acoustic sensors through a pressure hull serially and thereafter position the sensors side-by-side would be beneficial in underwater detection and tracking assemblies.

SUMMARY OF THE INVENTION

An object of the invention is to provide a device for supporting and carrying two units end-to-end such that the units may be passed through a relatively small orifice in a boundary layer and, thereafter, positioned side-by-side.

A further object of the invention is to provide such a device having means for rotatively moving one of the two units out of axial alignment with the other of the units and, thereafter, axially moving the one unit relative the other unit.

A still further object of the invention is to provide an endoscope for supporting and carrying two units, at least one of which is an electronic optical image sensor, end-to-end such that the units may be passed through a relatively small orifice in a mammal body and, thereafter, for positioning the units side-by-side.

A still further object of the invention is to provide a drive assembly for imparting rotative and axial movement to a rod affixed to one of the aforementioned units, whereby to effect rotational and axial translational movement of one unit relative to the other of the units.

With the above and other objects in view, as will hereinafter appear, a feature of the present invention is the provision of a device for carrying first and second units in aligned end-to-end disposition at the distal end of a shaft and for moving one of the units into position alongside the other of the units. The device comprises a base portion to which a proximal end of the shaft is fixed. A first of the two units is fixed to the distal end of the shaft and is in alignment with the shaft. A rod extends lengthwise through the shaft and through or alongside of a portion of the first unit, the rod being off-set from an axis of the shaft and being fixed at a distal end thereof to the second unit at a location removed from an axis of the second unit. The device is provided with means mounted on the base portion for effecting rotational movement of the rod to effect rotational movement of the second unit to a position removed from alignment with the first unit, and for effecting axial movement of the rod to effect axial movement of the second unit into the position alongside the first unit.

In accordance with a further feature of the invention, there is provided a device for carrying a unit on a distal end of a shaft and for moving the unit into position alongside the shaft. The device comprises a base portion to which a proximal end of the shaft is fixed. A rod extends lengthwise through the shaft, the rod being off-set from an axis of the shaft and being fixed at a distal end thereof to the unit at a location removed from an axis of the unit. Means are provided on the base portion for effecting rotational movement of the rod to effect rotational movement of the unit to a position removed from alignment with the shaft, and for effecting axial movement of the rod to effect axial movement of the unit into the position alongside the shaft.

In accordance with a further feature of the invention the device described hereinabove is an endoscope and at least one of the units comprises an electronic imaging sensor or video device.

In accordance with a still further feature of the invention, there is provided a drive assembly for imparting rotative and axial movement to a rod, the assembly comprising an elongated gear fixed to the rod and provided with circumferential grooves therein forming rings of rack teeth on the elongated gear, and with longitudinal grooves therein forming rows of pinion teeth on the elongated gear. Each of the teeth of the elongated gear is formed by intersections of the circular and longitudinal grooves, such that each tooth forms a portion of one of the rings and a portion of one of the rows. A first driving gear is engaged with the rows of pinion teeth for imparting the rotative movement to the elongated gear, and a second driving gear is engaged with the rings of rack teeth for imparting the axial movement to the elongated gear. Motive means are provided for turning the first and second driving gears, respectively.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings:

FIG. 7 is a perspective view of a portion of the unit moving mechanism, or drive assembly, of the device; and FIG. 8 is similar to FIG. 1, but illustrates an alternative embodiment.

DESCRIPTION OF THE PREFERRED EMBODIMENTS

Figure 1:
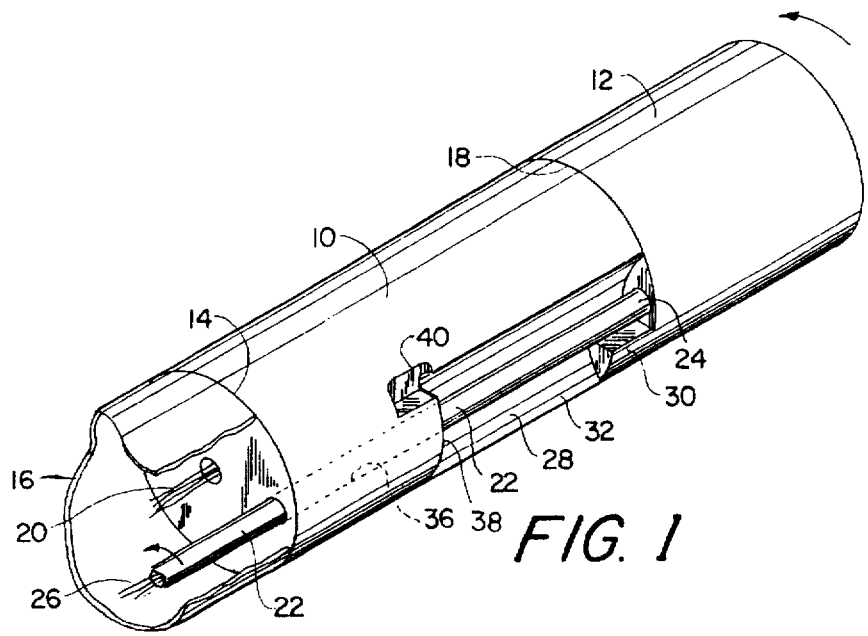
FIG. 1 is a perspective view of a pair of units mounted on a distal end of a shaft.

Referring to FIG. 1, it will be seen that in an illustrative embodiment of the invention there are provided first and second units 10, 12 mounted on a distal end 14 of a shaft 16. The first unit 10 is fixed to the shaft 16 in end-to-end relationship, and is of the same outer configuration and size as the shaft 16, typically cylindrical. The second unit 12 is adapted to be positioned in alignment with the first unit 10 as shown in FIG. 1, and is further adapted to be moved transversely of the first unit 10 (FIG. 2) and axially of the first unit 10 (FIG. 3), as will be further described hereinbelow. The second unit 12, at least at its proximal end 18, preferably is of the same outer configuration and size as the first unit 10, such that the assembly of shaft 16, first unit 10, and second unit 12, in aligned relationship, as illustrated in FIG. 1, may be passed through a boundary layer, such as the skin of a mammal body or a vehicle subject to unusually harsh environments, requiring as small an orifice as possible.

In one embodiment contemplated, the device illustrated in part in FIG. 1, comprises an endoscope in which the units 10, 12 are electronic imaging units, or are capsules for housing electronic imaging units. In such instances, electronic and fiber-optic leads, shown collectively at 20, may extend through the shaft 16 to the first unit 10 for the purpose of providing electrical connections to the electronic components of the imaging unit and transmitting light for illuminating the scene or site being viewed by the optical components of the imaging unit.

As used herein, the term "electronic imaging unit" comprises an electronic optical image sensor such as a CCD module and also one or more optical components for generating an optical image of the area under inspection and focusing that image onto the image sensor. The electronic imaging unit may also comprise additional mechanical and electronic components for operating the image sensor and generating an electrical video output signal representative of the scene or site being inspected. By way of example but not limitation, for the purposes of this invention the electronic imaging units may be like the ones disclosed and illustrated by said U.S. Pat. Nos. 4,832,003, 5,021,888, and 5,166,787. In the case of optical endoscopes, the unit 10 also may comprise optical fibers or rods for transmitting light to illuminate the scene or site being inspected.

A rod 22 extends through the shaft 16 and a portion of the first unit 10, and is, at its distal end 24, connected to the proximal end 18 of the second unit. When the units 10, 12 comprise optical image sensors, or other electronics or electrical devices, or means for illuminating the scene or site under inspection, the rod 22 may be a tubular member and have disposed therein further electronic and fiber-optic leads, identified collectively by the numeral 26, that extend to the second unit.

Figure 2:
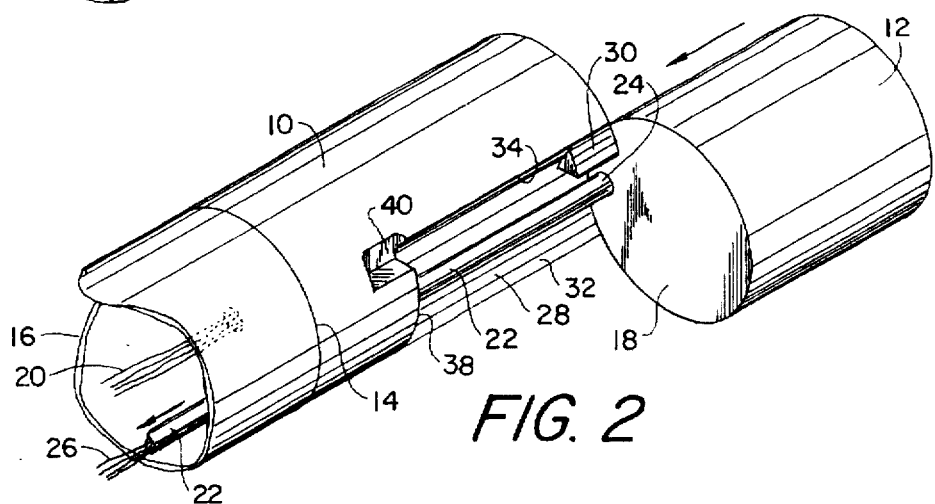
FIG. 2 is similar to FIG. 1, but shows one of the units moved rotatively out of alignment with the other of the units.

Referring to FIG. 2, it will be seen that rotation of the rod 22 on its axis causes corresponding rotative movement of the second unit 12 from the position shown in FIG. 1 to the position shown in FIG. 2. The rod 22 is off-set from the axis of the shaft 16 and is joined to the second unit 12 at a location off-set from the axis of the second unit. Accordingly, rotation of the rod 22 causes lateral translational movement of the second unit 12 to a position no longer aligned with the first unit 10, illustrated in FIG. 2.

The first unit 10 is provided with a groove 28 having a concave configuration complementary to the rounded configuration of the second unit 12, e.g., groove 28 has a circular curvature complementary to the circular curvature of the cylindrical outer surface of unit 12. The second unit 12 is provided with a detent 30 extending axially from the proximal end 18 of the second unit. When the second unit 12 is aligned with the first unit 10 (FIG. 1), the detent 30 extends into groove 28 and is engaged with a wall portion 32 of groove 28. In rotative movement of the second unit 12 (counterclockwise as seen in FIG. 1), the unit rotates until the detent 30 engages an opposite wall portion 34 of the groove 28 (FIG. 2). Thus, the detent 30 serves as a stop member, stopping rotative movement of the second unit 12 in its fully aligned position (FIG. 1) and in its transversely fully extended position (FIG. 2).

Figure 3:
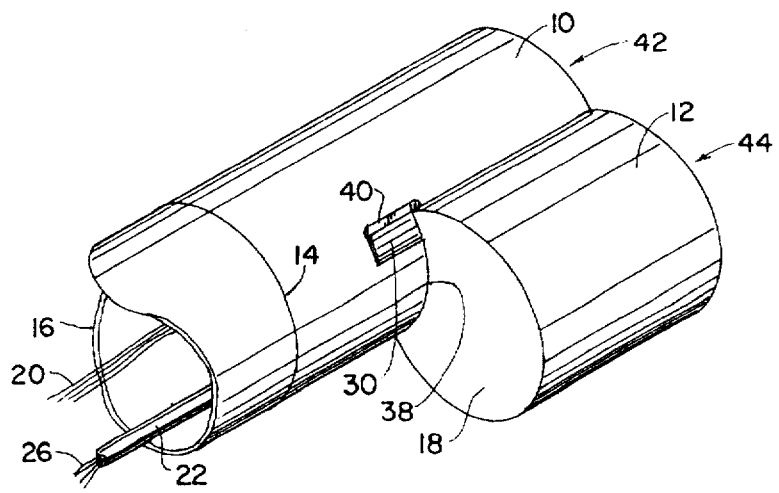
FIG. 3 is similar to FIG. 2, but shows the one unit moved axially to a position alongside the other unit.

The rod 22 is axially movable in the shaft 16 and in a bore 36 in the first unit 10. Once the second unit 12 is in the position illustrated in FIG. 2, then by axial movement of the rod 22 leftwardly, as viewed in FIG. 2, the second unit 12 may be slid along the groove 28 until the proximal end 18 of the second unit 12 abuts an end wall 38 of the groove 28, as shown in FIG. 3. As the second unit's proximal end 18 approaches the groove end wall 38, the detent 30 enters a substantially complementary-shaped notch 40 in unit 10 to foreclose the possibility of unwanted rotational movement. In this preferred embodiment, units 10, 12 are provided, respectively, with distal planar faces 42, 44 which, when the units 10, 12 are side-by-side as shown in FIG. 3, preferably are in a common plane transverse to the longitudinal axis of shaft 16.

In an embodiment contemplated, wherein the device herein is in the form of an endoscope, and wherein both units 10, 12 are electronic optical imaging units, such side-by-side positioning of the units provides for stereoscopic viewing of an internal region of a mammal body. In a further embodiment contemplated, wherein the device herein is an acoustic sensor, such side-by-side positioning of the units provides for range determination by triangulation. It will be appreciated that for some applications, it may be preferable for the units 10, 12 not to have their distal faces in a co-planar relationship, as, for example, where one unit is used to illuminate and/or observe a surgical work or the like that is being done by means carried by or inserted through the other unit, in which case it may be preferable to have the illuminating and/or observing unit offset rearwardly from the other unit.

Figure 4:
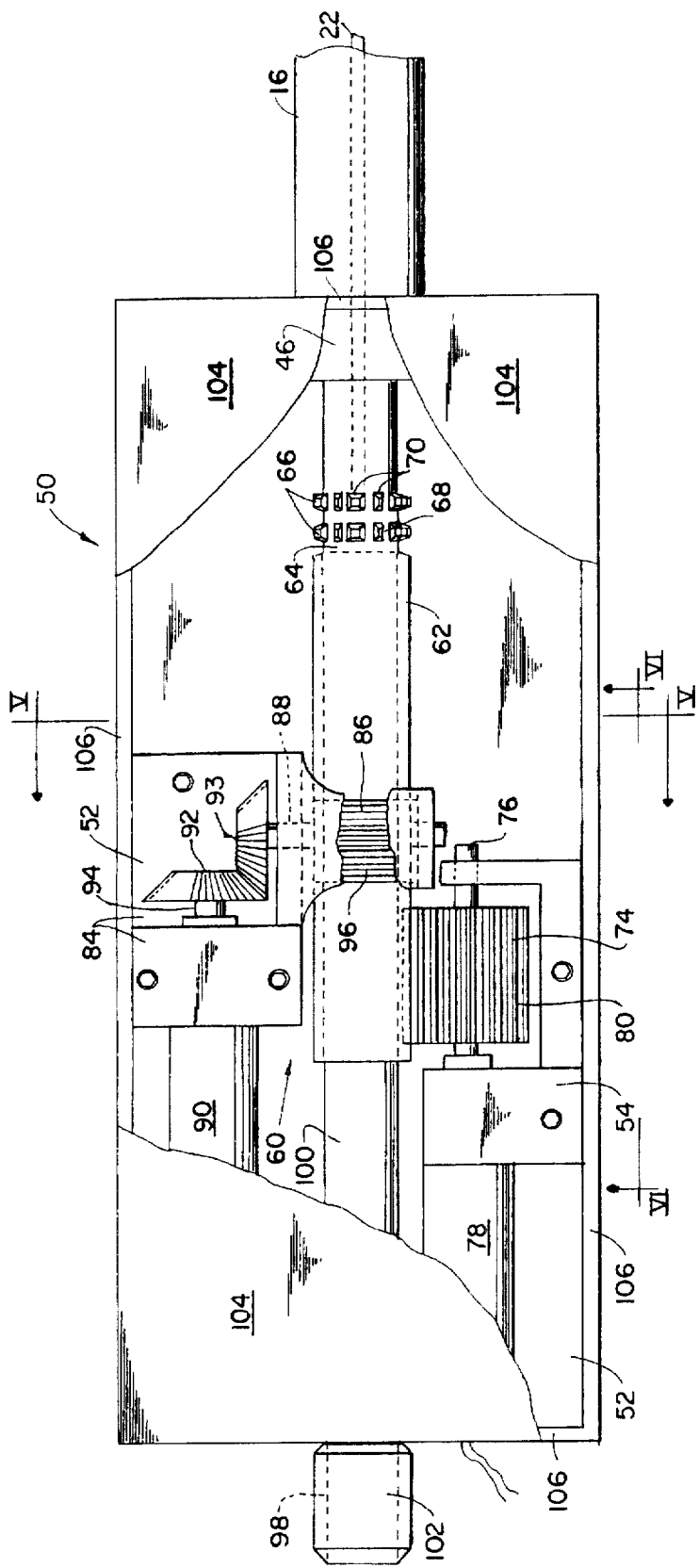
FIG. 4 is a top plan view, with portions broken away, of a base portion of the invention.
Figure 5:
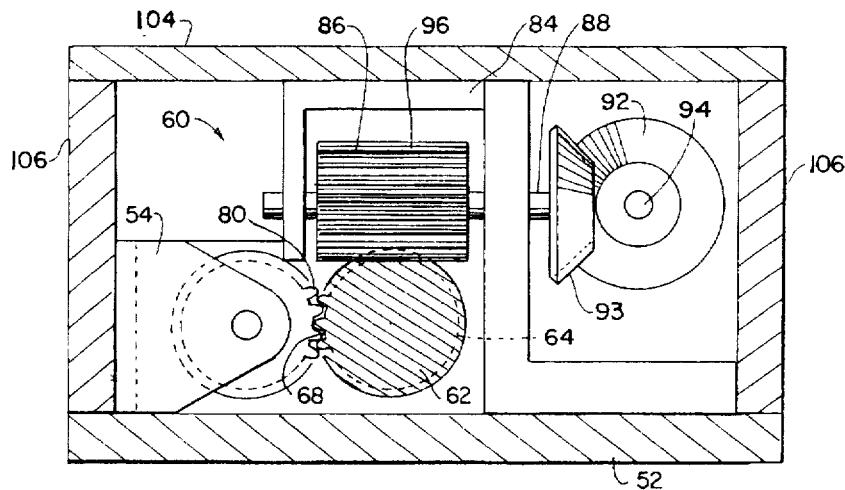
FIG. 5 is a sectional view taken along line V—V of FIG. 4.
Figure 6:
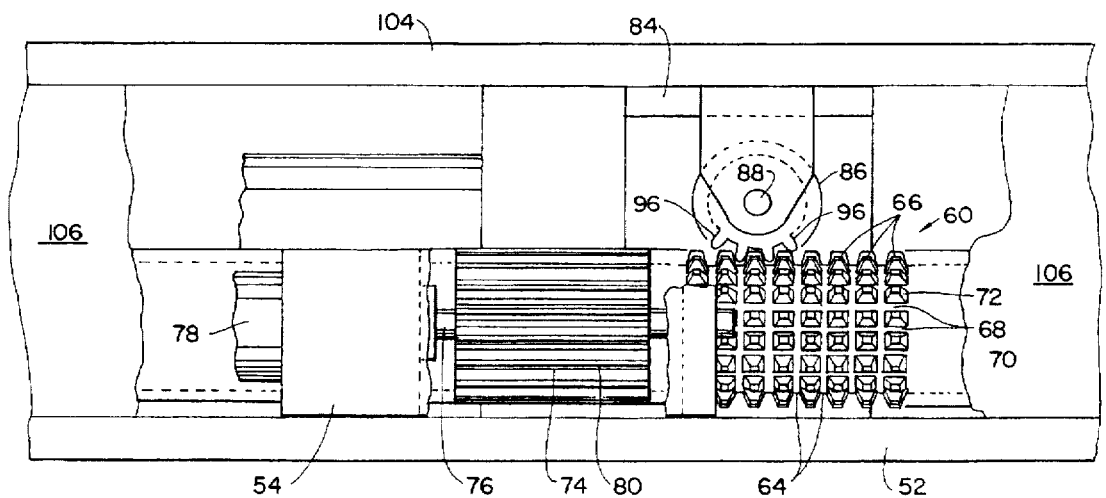
FIG. 6 is a side elevational view with portions broken away, taken along line VI—VI of FIG. 4.

Referring to FIG. 4, it will be seen that the illustrated instrument or device includes a base portion 50 to which a proximal end 46 of the shaft 16 is fixed. The base portion 50 may be shaped and sized to function as a handle whereby the device may be grasped and manipulated. The base portion 50 includes a base plate 52 on which is mounted a drive assembly 60 for imparting rotative and axial movement to the rod 22.

The drive assembly 60 includes an elongated two-way gear 62 (FIGS. 4-7). The gear 62 is provided with circumferentially-extending grooves 64 and longitudinally-extending grooves 68 that together result in formation of an array of teeth 72 arranged in rows formed by grooves 68 and rings (corresponding to columns in a row and column arrangement) formed by grooves 64. Viewed one way, grooves 64 subdivide the surface of gear 62 into a longitudinally-extending series of rack teeth, while the grooves 68 subdivide the same surface into a circular series of pinion teeth. Alternatively, the arrangement may be viewed as grooves 64 forming pinion gear teeth rings 66 while grooves 68 form rack gear teeth rows 70. Regardless, as may be seen in FIGS. 6 and 7, each tooth 72 formed by the intersecting of grooves 64, 68 forms a portion of one of the rings 66 and a portion of one of the rows 70. The essential thing is that the gear 62 provides an axially-extending array of parallel and closely spaced like pinion gears identified as rings 66 and a circular array of parallel and closely spaced like gear racks 70.

Mounted on base plate 52 is a U-shaped bracket means 54 that rotatably supports a shaft 76 on which is affixed a first driving gear 74. Shaft 76 is connected to and driven by a reversible electric motor 78 that is secured to base portion 50. In this preferred embodiment, the shaft 76 extends parallel to the gear 62. Gear 74 has a relatively large width (i.e., axial dimension) and has gear teeth 80 of substantially the same width that are arranged so as to mesh with successive rows 70 of teeth 72. Upon actuation of the motor 78, the first driving gear 74 is rotated and imparts rotation to gear 62. The gear 62 may be provided with a nose portion 82 in which is secured the rod 22 (FIGS. 4 and 7). Thus, rotation of gear 62 causes rotation of the rod 22, and thereby rotative movement of the second unit 12 (FIGS. 1-3), as described hereinabove.

Also mounted to base plate 52 is a second bracket means 84 (FIGS. 4-6) that rotatably supports a shaft 88 on which is fixed a second driving gear 86 having a plurality of gear teeth 96. Shaft 88 extends at a right angle to shaft 76 and gear 62. Teeth 96 mesh with successive rings 66 of teeth 72. Shaft 88 and in turn gear 86 are driven by a second reversible electric motor 90 that is fixed to bracket means 84.

For the sake of compactness of the drive assembly 60, the motor 90 is mounted so as to extend parallel to gear 62, with the result that two gears 92 and 93 (FIGS. 4 and 5) are employed to transmit rotation from electric motor shaft 94 to the second driving gear shaft 88. Gear 92 is affixed to the end of motor shaft 94 and gear 93 is affixed to the end of gear shaft 88. Upon actuation of motor 90, gears 92 and 93 cause the second driving gear 86 to rotate and engage successive rings 66 of teeth 72, thereby imparting axial movement to gear 62. Axial movement of gear 62 in turn causes axial translation of rod 22, and thereby the second unit 12 (FIGS. 1-3), as described hereinabove.

Formed integral with or otherwise affixed to the proximal end of gear 62 is a rod 100 having a knob 102, or other manual means, whereby an axial and/or a rotational force may be applied to rod 100 so as to cause gear 62 and thereby rod 22 and the second unit 12, to move axially, and/or rotate. At least in the case of endoscopes where the electrical motors 78 and 90 are relatively small, the inertial and frictional resistance to turning exhibited by motors 78 and 90, respectively, is not excessive, being low enough to be overcome by a manually applied force but sufficient to provide a steadying restraint to axial or rotative movement of gear 62.

It should be appreciated that each of the two modes of motion (axial and rotational) offered by drive assembly 60 does not impede or cause the other mode of motion, i.e., rotational motion does not inhibit or cause axial motion, and vice versa. Also, both modes of motion can be achieved simultaneously, and at different rates.

Thus, the drive assembly 60 provides electrically powered discrete motive means 78, 90 for selectively moving a single actuating gear 62 rotatively or axially, and provides a single manual means 100, 102 by which the two movements may be effected manually. The drive assembly motive means 78, 90 may be operated by a power source (not shown) located externally of the device or by a battery power source mounted to base portion 50. The manual manipulation option afforded by means 100,102 is advantageous in the event of a power or other failure.

Attached to base portion 50 are a top plate 104 and side walls 106 (FIG. 5) which coact to form a housing for concealing the drive system for rod 22. That resulting housing also serves as a handle by which the entire unit may be held. Alternatively, a pistol grip or other grip means (not shown) may be fixed to the base portion for grasping and manipulating the device.

It is contemplated that the first unit 10, described hereinabove as a discrete unit affixed to the shaft 16, instead may comprise a hollow end portion 10a of the shaft 16, as shown in FIG. 8. In the latter case, the first unit contained by the end portion 10a may be a discrete video unit comprising an electronic image sensor, an optical system (comprising at least an objective lens) for focusing an image of a scene or site being viewed onto the image sensor, and illuminating means for illuminating the scene or site. Optionally, the end portion 10a may serve simply as a conduit for introducing a surgical instrument to the surgical site. It also is contemplated that the end portion 10a may serve as a housing for an electronic acoustic energy-sensing unit.

The outer configuration and size of the first unit 10 may be different than that of shaft 16, and the second unit 12 need not have the same size and configuration as first unit 10 or shaft 16. It also is contemplated that shaft 16 and rod 22 may be flexible instead of rigid or stiff.

It is to be understood that the present invention is by no means limited to the particular construction or modification herein disclosed and/or shown in the drawings, but also comprises other modifications or equivalents within the scope of the claims.

Having thus described our invention, what we claim as new and desire to secure by Letters Patent of the United States is:

1. A device comprising:
    first and second observation units adapted to be in aligned end-to-end disposition;
    a shaft for supporting said first and second units at a distal end of said shaft, said first unit being fixed to said distal end of said shaft and in alignment with said shaft;
    a rod for moving said second unit into position alongside said first unit, said rod extending lengthwise through said shaft and through a portion of said first unit, said rod being off-set from an axis of said shaft and being fixed at a distal end thereof to said second unit at a location removed from an axis of said second unit;
    a base portion to which a proximal end of said shaft is fixed; and
    means for (a) effecting rotational movement of said rod to effect rotational movement of said second unit to a position removed from alignment with said first unit, and (b) effecting axial movement of said rod to effect axial movement of said second unit into another position alongside said first unit, wherein said means for effecting rotational and axial movement of said rod comprises a two-way gear fixed to said rod, said gear being drivable rotatively and axially, a first driving gear mounted on said base portion for rotatively driving said two-way gear, a second driving gear mounted on said base portion for axially driving said two-way gear, and power means mounted on said base portion for selectively rotating said first and second driving gears.

2. A device in accordance with claim 1 wherein said two-way gear forms an extension of said rod, and further wherein said means for effecting rotational and axial movement of said rod further comprises grip means connected to said rod for manually turning and/or axially moving said two-way gear and thereby said rod, said power means providing limited frictional resistance to manual turning and axial movement of said two-way gear, and thereby a steadying resistance to said turning and axial movement of said rod.

3. A device in accordance with claim 1 wherein said two-way gear is provided with circular grooves forming rack teeth and with longitudinal grooves forming pinion teeth, said first driving gear being engaged with said pinion teeth to effect said rotational driving of said two-way gear, and said second driving gear being engaged with said rack teeth to effect axial driving of said two-way gear.

4. A device in accordance with claim 1 wherein said power means comprises first and second electrical motors for driving said first and second driving gears respectively.

5. A device in accordance with claim 4 wherein said electrical motors are reversible.

6. A device in accordance with claim 1 wherein said first unit is provided with a concave groove and said rod extends lengthwise of said first unit in said groove, said groove having a curvature substantially equal to the curvature of said second unit, whereby said groove is configured to receive said second unit as said second unit is drawn axially into said groove by said rod as said second unit is moved into position alongside said first unit.

7. A device in accordance with claim 1 wherein said device comprises an endoscope and at least one of said first and second units comprises an image sensor.

8. A device in accordance with claim 7 wherein said base portion includes a handle component.

9. A device in accordance with claim 1 wherein said first and second units are provided with face surfaces which, when one of said units is alongside the other of said units, are in a common distal plane transverse to a longitudinal axis of said shaft.

10. A device in accordance with claim 1 further including means attached to said base portion for forming a housing for said power means.

11. A device according to claim 1 wherein each of said first and second observation units comprises an electronic optical image sensor for sensing optical images and producing electrical signals representative of said optical images, and optical means for generating an optical image of an area under observation and focusing that image onto said electronic optical image sensor.

12. A device according to claim 11 wherein said electronic optical image sensor comprises a CCD.

13. A device comprising:
    first and second observation units adapted to be in aligned end-to-end disposition;
    a shaft for supporting said first and second units at a distal end of said shaft, said first unit being fixed to said distal end of said shaft and in alignment with said shaft;
    a rod for moving said second unit into position alongside said first unit, said rod extending lengthwise through said shaft and through a portion of said first unit, said rod being off-set from an axis of said shaft and being fixed at a distal end thereof to said second unit at a location removed from an axis of said second unit;
    a base portion to which a proximal end of said shaft is fixed; and
    means for (a) effecting rotational movement of said rod to effect rotational movement of said second unit to a position removed from alignment with said first unit, and (b) effecting axial movement of said rod to effect axial movement of said second unit into another position alongside said first unit;
    wherein said first unit is provided with a concave groove and said rod extends lengthwise of said first unit in said groove, said groove having a curvature substantially equal to the curvature of said second unit, whereby said groove is configured to receive said second unit as said second unit is drawn axially into said groove by said rod as said second unit is moved into said position alongside said first unit; and
    wherein said first unit is provided with a notch extending from said groove, and said second unit is provided with a detent configured to be snugly received by said notch when said second unit is in said position alongside said first unit to prevent rotative movement of said second unit in said position alongside said first unit.

14. A device in accordance with claim 13 wherein said detent extends from an end of said second unit and is adapted to extend into said groove of said first unit and serves as a stop member to limit rotative movement of said second unit relative to said first unit.

15. A device according to claim 13 wherein each of said first and second observation units comprises an electronic optical image sensor for sensing optical images and producing electrical signals representative of said optical images, and at least one optical component for generating an optical image of an area under observation and focusing that image onto said electronic optical image sensor.

16. A device comprising:

a base portion;

a shaft fixed at a proximal end thereof to said base portion;

a discrete unit on a distal end of said shaft;

a rod extending lengthwise through said shaft, said rod being offset from an axis of said shaft and being fixed at a distal end thereof to said unit at a location removed from an axis of said unit; and means on said base portion for effecting rotational movement of said rod to effect rotational movement of said unit to a position removed from alignment with said shaft, and for effecting axial movement of said rod to effect axial movement of said unit into a position alongside said shaft;

wherein said means for effecting rotational and axial movement of said rod comprises a two-way gear mounted on said base portion and fixed to said rod, said gear being drivable rotationally and axially, a first driving gear mounted on said base portion for rotatively driving said two-way gear, a second driving gear mounted on said base portion for axially driving said two-way gear, and power means mounted on said base portion for selectively energizing said first and second driving gears.

17. A device in accordance with claim 16 wherein said means for effecting rotational and axial movement of said rod further comprises grip means on said rod for manual turning of said rod and for moving said rod axially, said driving gears providing frictional resistance to said manual turning and axial movement of said two-way gear, and thereby a steadying resistance to said turning and axial movement of said rod.

18. A device in accordance with claim 16 wherein said two-way gear is provided with circular grooves forming rack teeth and with longitudinal grooves forming pinion teeth, said first driving gear being engaged with said pinion teeth to effect said rotative driving of said two-way gear, and said second driving gear being engaged with said rack teeth to effect said axial driving of said two-way gear.

19. A device in accordance with claim 16 wherein said power means comprises first and second discrete motors for driving said first and second driving gears respectively.

20. A device according to claim 16 wherein said discrete unit is a video device comprising optical means for generating an optical image of an area under observation, and an electronic optical image sensor for sensing said optical image and producing electrical output signals representative of said optical image.

21. A device comprising:

a base portion;

a shaft fixed at a proximal end thereof to said base portion;

a discrete unit on a distal end of said shaft;

a rod extending lengthwise through said shaft, said rod being offset from an axis of said shaft and being fixed at a distal end thereof to said unit at a location removed from an axis of said unit; and means on said base portion for effecting rotational movement of said rod to effect rotational movement of said unit to a position removed from alignment with said shaft, and for effecting axial movement of said rod to effect axial movement of said unit into a position alongside said shaft;

wherein said means for effecting rotational and axial movement of said rod comprises grip means on said rod for manually turning said rod and for moving said rod axially;

wherein said shaft is provided with a groove in a periphery thereof, and said rod extends lengthwise of said shaft in said groove, said groove having a configuration substantially complementary to the configuration of said unit, said groove being thereby configured to receive said unit as said unit is drawn axially into said groove by said rod to be placed in said position alongside said shaft; and wherein said shaft is provided with a notch extending from said groove, and said unit is provided with a detent configured to be snugly received by said notch when said unit is in said position alongside said shaft to prevent rotative movement of said unit in said position alongside said shaft.

22. A device in accordance with claim 21 wherein said detent extends from an end of said unit and is adapted to extend into said groove of said shaft and serves as a stop member to limit rotative movement of said unit relative to said shaft.

23. A device according to claim 21 wherein said discrete unit comprises an electronic optical image sensor for sensing optical images and producing electrical output signals representative of said optical images, and optical means for generating an image of an area under observation and focusing that image onto said electronic optical image sensor.

24. A drive assembly for imparting rotative and axial movement to a member, the assembly comprising:

an elongated gear adapted to be coupled to the member and provided with circular grooves therein forming rings of rack teeth on said elongated gear, and with longitudinal grooves therein forming rows of pinion teeth on said elongated gear;

each of said teeth of said elongated gear being formed by intersections of said circular and longitudinal grooves, such that each of said teeth forms a portion of one of said rings and a portion of one of said rows;

a first driving gear engaged with said rows of pinion teeth for imparting said rotative movement to said elongated gear;

a second driving gear engaged with said rings of rack teeth for imparting said axial movement to said elongated gear; and discrete first and second motive means for turning said first and second driving gears, respectively.

25. A drive assembly in accordance with claim 24, wherein said assembly further comprises grip means fixed to said elongated gear, by which an operator may manually move said elongated gear rotatively and axially.

* * * * *